US009776170B2

(12) United States Patent
Kaminsky et al.

(10) Patent No.: US 9,776,170 B2
(45) Date of Patent: Oct. 3, 2017

(54) HETEROGENEOUS ALKANE DEHYDROGENATION CATALYST

(71) Applicant: Dow Global Technologies LLC, Midland, MI (US)

(72) Inventors: Mark P. Kaminsky, Friendswood, TX (US); Andrzej Malek, Midland, MI (US); Lin Luo, Sugar Land, TX (US); Brien A. Stears, League City, TX (US); Isa K. Mbaraka, Lake Jackson, TX (US); Devon C. Rosenfeld, Freeport, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/035,315

(22) PCT Filed: Dec. 2, 2014

(86) PCT No.: PCT/US2014/068007
§ 371 (c)(1),
(2) Date: May 9, 2016

(87) PCT Pub. No.: WO2015/094631
PCT Pub. Date: Jun. 25, 2015

(65) Prior Publication Data
US 2016/0288093 A1 Oct. 6, 2016

Related U.S. Application Data

(60) Provisional application No. 61/916,393, filed on Dec. 16, 2013.

(51) Int. Cl.
*B01J 21/08* (2006.01)
*B01J 21/04* (2006.01)
*B01J 21/12* (2006.01)
*B01J 23/08* (2006.01)
*B01J 37/02* (2006.01)
*C07C 5/333* (2006.01)

(52) U.S. Cl.
CPC .......... *B01J 23/08* (2013.01); *B01J 37/0201* (2013.01); *B01J 37/0215* (2013.01); *B01J 37/0236* (2013.01); *B01J 37/0242* (2013.01); *C07C 5/3332* (2013.01); *C07C 2521/02* (2013.01); *C07C 2521/04* (2013.01); *C07C 2521/12* (2013.01); *C07C 2523/08* (2013.01); *Y02P 20/52* (2015.11)

(58) Field of Classification Search
CPC ... B01J 23/08; B01J 21/04; B01J 21/08; B01J 21/12; B01J 2523/31; B01J 2523/32; B01J 2531/31; B01J 2531/32; C07C 2521/04; C07C 2521/08; C07C 2521/12; C07C 2523/08

USPC ....... 502/238, 355, 527.12, 527.15; 423/633, 423/640, 642; 428/403; 501/94, 133, 501/153, 154
See application file for complete search history.

(56) References Cited

U.S. PATENT DOCUMENTS

| 2,454,227 | A | * | 11/1948 | Beeck | B01J 21/16 423/600 |
| 3,198,749 | A | | 8/1965 | Gladrow | |
| 3,506,561 | A | * | 4/1970 | Caesar | H01M 4/86 204/290.01 |
| 3,758,418 | A | * | 9/1973 | Leonard, Jr. | B01J 37/024 423/592.1 |
| 3,926,781 | A | * | 12/1975 | Gale | B01J 23/08 208/117 |
| 4,052,738 | A | * | 10/1977 | Hosomi | C04B 41/009 204/192.15 |
| 4,056,575 | A | * | 11/1977 | Gregory | C07C 15/00 208/135 |
| 4,056,576 | A | * | 11/1977 | Gregory | B01J 23/08 585/415 |
| 4,180,689 | A | * | 12/1979 | Davies | B01J 29/061 208/135 |
| 5,073,658 | A | * | 12/1991 | Saleh | B01J 21/12 502/242 |
| 5,308,822 | A | * | 5/1994 | Iezzi | B01J 23/02 502/243 |
| 5,414,182 | A | | 5/1995 | Iezzi et al. | |
| 6,031,143 | A | | 2/2000 | Buonomo et al. | |
| 6,177,381 | B1 | * | 1/2001 | Jensen | B01J 23/40 428/403 |
| 7,235,706 | B2 | | 6/2007 | Iezzi et al. | |
| 7,473,668 | B2 | * | 1/2009 | Bartolini | B01J 23/34 502/263 |

(Continued)

FOREIGN PATENT DOCUMENTS

| CN | 1467025 | * | 1/2004 | ............. B01D 53/56 |
| IT | EP 0560437 A1 | * | 9/1993 | ............. B01J 23/02 |
| JP | 2001240401 A | | 9/2001 | |

OTHER PUBLICATIONS

"Influence of the preparation method on the surface properties and activity of alumina-supported gallium oxide catalysts," Alice Luminita Petre et al. Studies in Surface Science and Catalysis 143 (2002), pp. 747-755.*
"Selective catalytic reduction of No with C1-C3 reductants over solvothermally prepared Ga2O3—Al2O3 catalysts: Effects of water vapor and hydrocarbon uptake," Yuya Miyahara et al. Applied Catalysis B: Environmental 84 (2008), pp. 289-296.*
"Direct formation of spinel-structured y-Ga2O3—Al2O3 nanoparticles by a mild hydrothermal method," Masanori Hirano et al. Ceramics International 41 (2015), pp. 14285-14292.*

(Continued)

*Primary Examiner* — Patricia L Hailey
(74) *Attorney, Agent, or Firm* — Dinsmore & Shohl LLP

(57) ABSTRACT

A heterogeneous catalyst suitable for use in alkane dehydrogenation has an active layer that includes alumina and gallia. The active layer is dispersed on a support such as alumina or silica-modified alumina.

14 Claims, No Drawings

(56) References Cited

U.S. PATENT DOCUMENTS

| | | | | |
|---|---|---|---|---|
| 8,653,317 | B2* | 2/2014 | Pierce | B01J 23/62 585/435 |
| 2006/0094595 | A1* | 5/2006 | Labarge | B01D 53/945 502/325 |
| 2007/0123418 | A1* | 5/2007 | Han | B01D 53/945 502/339 |
| 2013/0079578 | A1 | 3/2013 | Yang et al. | |
| 2014/0200385 | A1 | 7/2014 | Pretz et al. | |

OTHER PUBLICATIONS

"Performance of y-Ga2O3—Al2O3 solid solutions prepared by spray pyrolysis for CH4—ScR of NO," Tsunenori Watanabe et al. Applied Catalysis A: General 396 (2011), pp. 140-147.*

"Hydrolytic decomposition of CF4 over alumina-based binary metal oxide catalysts: high catalytic activity of gallia-alumina catalyst," Zeinhom Mohamed El-Bahy et al. Catalysis Today 90 (2004), pp. 283-290.*

"Dehydrogenation of propane over spinel-type gallia-alumina solid solution catalysts," Miao Chen et al. Journal of Catalysis 256 (2008), pp. 293-300.*

"In Situ Fourier Transform Infrafred Study of the Selection Reduction of NO with Propene over Ga2O3—Al2O3," Masaaki Haneda et al. Journal of Catalysis 206 (2002), pp. 114-124.*

Shen, Miao, et.al., "Dehydrogenation of propane over spinel-type gallia-alumina solid solution Catalysts" Journal of Catalysis, 2008, vol. 256, p. 293-300.

PCT/US2014/068007, International Search Report and Written Opinion dated Mar. 9, 2015.

PCT/US2014/068007, International Preliminary Report on Patentability dated May 10, 2016.

PCT/US2014/068007, Response Written Opinion dated Oct. 6, 2015.

PCT/US2014/068007, Second Written Opinion dated Jan. 19, 2016.

Damyanov, S. et. al. "Surface Characterization of Zirconia-Coated Alumina and Silica Carriers" Journal of Catalysis 168, 421-430 (1997.

Boger, Thorsten "Monolithic Catalysts for the Chemical Industry" Ind. Eng. Chem. Res. 2004, 43, 4602-4611.

Gaspar, A.B. "Distribution of chromium species in catalysts supported on ZrO2/Al2O3 and performance in dehydrogentation" Journal of Catalysis, 220 309-316, (2003).

Nakagawa, Kiyoharu et. al. "Promoting effect of carbon dioxide on the dehydrogentation and aromatization of ethane over gallium-loaded catalysts" Catalysis Letters, 64 215-221, (2000).

* cited by examiner

HETEROGENEOUS ALKANE DEHYDROGENATION CATALYST

The present application claims the benefit of U.S. Provisional Application No. 61/916,393, filed on Dec. 16, 2013.

This invention relates generally to a heterogeneous alkane dehydrogenation catalyst, particularly a heterogeneous alkane dehydrogenation catalyst wherein at least two metal oxides are dispersed on a catalyst support, more particularly a heterogeneous alkane dehydrogenation catalyst wherein two metal oxides are dispersed on a metal oxide catalyst support and one of the metals in the dispersed metal oxides is the same as the metal in the metal oxide catalyst support, and still more particularly heterogeneous alkane dehydrogenation that comprises, consists essentially of or consists of a combination of gallium oxide ($Ga_2O_3$) and aluminum oxide ($Al_2O_3$) on an alumina ($Al_2O_3$)-containing support.

In a typical $Ga_2O_3$ on $Al_2O_3$ heterogeneous alkane dehydrogenation catalyst, the active component, $Ga_2O_3$, is deposited, e.g. by a known technique such as aqueous impregnation, using a suitable $Ga_2O_3$ precursor (e.g. a salt such as a nitrate) on a surface of the $Al_2O_3$ or silica-modified alumina ($SiO_2$—$Al_2O_3$) support and then calcined to form an active $Ga_2O_3$ layer on the $Al_2O_3$ support.

As used herein, a silica-modified alumina support preferably has a silica content within a range of from greater than 0 wt % to less than 10 wt %, based on total weight of the support. A silica-modified alumina support is not a zeolite.

This invention demonstrates an improvement over the typical $Ga_2O_3$ on $Al_2O_3$ heterogeneous alkane dehydrogenation catalyst. The improvement comprises depositing an $Al_2O_3$ precursor on the surface of the $Al_2O_3$ or $SiO_2$—$Al_2O_3$ support, before, after or, preferably, in conjunction with depositing the $Ga_2O_3$ precursor on the surface of said support (also known as "co-depositing", "co-loading" or "co-deposition"). Following calcination subsequent to deposition of both the $Al_2O_3$ precursor and the $Ga_2O_3$ precursor, the catalyst has an active layer that comprises both $Ga_2O_3$ and $Al_2O_3$. For a discussion of impregnation techniques and co-loading, see *Catalyst Handbook, 2nd Edition*, edited by Martyn V. Twygg, Oxford University Press, ISBN 1-874545-36-7, and Pure & Appl. Chem., Vol. 67, Nos 8/9, pp. 1257-1306, 1995).

PCT Application (WO) 2010/107591 (Luo et al.) discloses a supported paraffin dehydrogenation catalyst that comprises a first component selected from tin, germanium, lead, indium, Ga, thallium and compounds thereof, a second component selected from Group VIII of the Periodic Table (e.g. platinum (Pt), palladium, iron, ruthenium, osmium, cobalt, rhodium, iridium or nickel), an alkali metal or alkaline earth metal or a compound thereof, and a support comprising $Al_2O_3$ in gamma crystalline form.

M. Chen et al., in "Dehydrogenation of propane over spinel-type Gallia-alumina solid solution catalysts", *Journal of Catalysis* 256 (2008) pages 293-300, discloses dehydrogenation of propane to propylene over a series of mixed $Ga_xAl_{10-x}$ oxides (x varying from 0 to 10). In summarizing literature for $Ga_2O_3$-based catalysts, M. Chen et al. refers to $Ga_2O_3$ catalysts that are dispersed on an inert oxide support such as titania ($TiO_2$) or $Al_2O_3$. M. Chen et al. appears to equate solid solutions to bulk metal oxide catalysts.

B. Xu et al., in "Support effect in dehydrogenation of propane in the presence of $CO_2$ over supported gallium oxide catalysts", *Journal of Catalysis* 239 (2006) pages 470-477, teaches dehydrogenation of propane to propene (propylene) in the absence or presence of $CO_2$ over different supported $Ga_2O_3$ catalysts including $Ga_2O_3/TiO_2$, $Ga_2O_3/Al_2O_3$, $Ga_2O_3/ZrO_2$, $Ga_2O_3/SiO_2$ and $Ga_2O_3/MgO$, the latter two being ineffective for dehydrogenation of propane. Supported catalysts are prepared by impregnating a Ga precursor solution onto the second named oxide, e.g. $TiO_2$.

C. Areád et al, in "Synthesis and Characterization of Spinel-Type Gallia-Alumina Solid Solutions", Z. Anorg. Allg. Chem 2005, 631, pages 2121-2126, presents teachings relative to mixed $Ga_2O_3$—$Al_2O_3$ oxides that are solid solutions (bulk catalysts) with Ga:Al ratios between 9:1 and 1:9 that have utility in hydrocarbon dehydrogenation.

U.S. Pat. No. 4,056,576 (Gregory et al.) relates to a process for dehydrogenating saturated hydrocarbons in the presence of a Ga catalyst (elemental Ga or a Ga compound deposited on a support) to produce unsaturated hydrocarbons. The support may be $Al_2O_3$ or $SiO_2$ with or without surface hydroxyl groups that may be exchanged by ions of metals selected from Ga, Al, iron and nickel.

EP 0 905 112 (Buonomo et al.) relates to production of styrene starting from benzene and ethane using a dehydrogenation catalyst such as one based on Ga and platinum (Pt) on $Al_2O_3$ in delta or theta phase or in a mixture of delta+theta, theta+alpha or delta+theta+alpha phases.

European Patent Publication (EP) 0441430 (Iezzi et al.) discloses a process for catalytically dehydrogenating a two to five carbon atom ($C_2$-$C_5$) paraffin using a supported catalyst composition consisting of Pt, tin, and a supporting substrate selected from titanated $Al_2O_3$, titanated $SiO_2$ and/or titanium silicate.

U.S. Pat. No. 3,198,749 (Gladrow et al.) relates to a $SiO_2$—$Al_2O_3$—$Ga_2O_3$ catalyst and its preparation.

U.S. Pat. No. 5,308,822 and its divisional U.S. Pat. No. 5,414,182 (both Iezzi et al.) provide a process for activating a catalytic composition for paraffin dehydrogenation that contains Ga, $Al_2O_3$ and, optionally $SiO_2$ and/or one or more alkali metals or alkaline earth metals.

U.S. Pat. No. 7,235,706 (Iezzi et al.) relates to a process for preparing light olefins from corresponding paraffins by reacting the paraffins in a reactor with a catalytic system containing Ga, Pt, optionally one or more alkali metals or alkaline earth metals and a $SiO_2$—$Al_2O_3$ support. Preferred procedures include impregnation by incipient wetness or immersing the support in a solution containing the precursors.

Bulk metal oxide alkane dehydrogenation catalysts prepared by, for example, a sol-gel procedure tend to have a selectivity to desired olefins lower than desired, even with a high loading of Ga on the order of 20 weight percent (wt %), based on total catalyst weight. Such a high loading makes the catalyst much more expensive than a lower loading on the order of, for example, three wt % to five wt %. In addition, the bulk metal oxide catalysts have physical properties such as density and attrition resistance that are often less than desired due, at least in part, to an inability to adjust such properties independent of the bulk composition that necessarily includes the active component(s) (e.g. Ga). By way of contrast, the support used in preparing a supported catalyst can be designed and prepared to optimize relevant properties such as stability, density or attrition resistance independent of the active component(s).

Bulk metal oxide catalysts tend to use active components (e.g. $Ga_2O_3$) less efficiently than supported mixed metal oxide catalysts as the bulk catalysts must, as skilled artisans understand them, have the active component distributed throughout the catalyst. This distribution effectively makes a significant portion of the active component inaccessible for catalytic service.

As compared to such bulk metal oxide alkane dehydrogenation catalysts, supported alkane dehydrogenation catalysts such as $Ga_2O_3$ disposed on a catalyst support (e.g. $Al_2O_3$ or $SiO_2$—$Al_2O_3$) offer more economical utilization of the active component ($Ga_2O_3$) without substantially sacrificing desirable physical characteristics of the support material (e.g. attrition resistance and density).

Skilled artisans seek improvements in catalyst stability and performance irrespective of whether the catalyst is a bulk metal oxide catalyst or a supported metal oxide catalyst (e.g. supported $Ga_2O_3$ catalyst).

In some aspects, this invention is a heterogeneous alkane dehydrogenation catalyst consisting of a combination of a) both aluminum oxide and gallium oxide dispersed as an active layer on (or onto) b) an alumina support or a silica-modified alumina support. Such catalysts have utility in dehydrogenating alkanes such as propane to produce propylene.

In some aspects, this invention is a process for preparing such a heterogeneous alkane dehydrogenation catalyst, which process comprises loading precursors to $Ga_2O_3$ and $Al_2O_3$ simultaneously or sequentially onto an $Al_2O_3$ support or a $SiO_2$—$Al_2O_3$ support. Following completion of the gallium oxide and aluminum oxide precursor loading, calcine the loaded support. Calcining occurs at a temperature sufficient to decompose the metal precursor, such temperature being at least 400° C., preferably at least 550° C. and most preferably at least 700° C. Calcining occurs at a temperature below 1100° C., preferably less than 1000° C.

The heterogeneous alkane dehydrogenation catalyst comprises, consists essentially of or consists of an inactive support that has an active layer comprising, consisting essentially of or consisting of Ga and Al, preferably in the form of $Ga_2O_3$ and $Al_2O_3$, dispersed thereon. The active layer has a molar ratio of Ga to Al within a range of from greater than 0.5:1 to less than 15:1, preferably from 1:1 to 10:1 and more preferably from 1.5:1 to 5:1. Ga, expressed as $Ga_2O_3$, on the support and in the active layer, is present in an amount within a range of from less than 14 wt %, more preferably less than 10 wt % and still more preferably less than 5 wt %, in each case greater than 0 wt % and based on total catalyst weight. Al, expressed as $Al_2O_3$, on the support and in the active layer, is present in an amount within a range of from 0.05 wt % to 10 wt %, preferably from 0.05 wt % to 5 wt %, each wt % being based upon total catalyst weight. The support is preferably substantially free of Ga and more preferably completely free of Ga prior to having the active layer dispersed thereon. The support is preferably selected from $Al_2O_3$ and $SiO_2$—$Al_2O_3$. The $SiO_2$—$Al_2O_3$ has a $SiO_2$ content within a range of from 0.1 wt % to 10 wt %, preferably from 0.1 wt % to 5 wt %, in each case based upon total weight of the support.

The above heterogeneous alkane dehydrogenation catalyst has a dehydrogenation performance that exceeds that of comparative catalysts such as a bulk mixed oxide catalyst or a supported catalyst wherein only $Ga_2O_3$ is dispersed as a supported metal oxide.

$Ga_2O_3$ precursors are suitably selected from soluble gallium salts, such as gallium (III) nitrate, gallium (III) acetylacetonate, gallium (III) chloride, with gallium (III) nitrate being preferred.

$Al_2O_3$ precursors are suitably selected from soluble aluminum salts, such as aluminum (III) nitrate, aluminum (III) acetylacetonate, aluminum (III) chloride, with aluminum (III) nitrate being preferred.

COMPARATIVE EXAMPLES (CEX) A THROUGH C

In a replication of work presented by Chen et al. in the 2008 Journal of Catalysis article noted above, mix together concentrated aqueous ammonia (28 wt % ammonia, Aldrich, Catalogue No. 221228, based upon total weight of concentrated aqueous ammonia) and ethanol in a 50:50 volume ratio. Add this mixture dropwise to an ethanol solution of gallium nitrate hydrate (99.9 percent purity, Aldrich, Catalogue No. 289892) and aluminum nitrate hydrate (at least 98 percent purity, Aldrich, Catalogue No. 237973) until solution pH reaches 8.5 and no further visible precipitation is observed. The ethanol solutions each contain 15 grams (g) of gallium nitrate hydrate and varying amounts of aluminum nitrate hydrate, with CEx A containing 13.2 g, CEx B containing 6.6 g, and CEx C containing 3.3 g. Filter gel from the solution and wash the gel with ethanol before drying it overnight at 373° Kelvin (100° C.) and then calcining it at 773° K (500° C.) for six hours.

EX 1-5 AND CEX D-E

Use aqueous incipient wetness impregnation to prepare a supported catalyst using 20 g of SIRALOX™ 1.5/70 (Sasol, 1.5 wt % silica, based on total weight of the support, and a surface area (S.A.) of 79 square meters per gram ($m^2/g$) as a catalyst support. Pre-dry the catalyst support at a temperature of 350° C. for a period of two hours. Spray a solution with a targeted amount of metal precursor (gallium nitrate hydrate and aluminum nitrate as in CEx A-C and potassium nitrate (at least 99% purity, Aldrich, Catalogue No. 221295) and solution volume sufficient to match 95% pore volume (PV) (0.25 milliliters per gram (mL/g) onto the pre-dried support. Age the sprayed support at ambient temperature for two hours before drying it in an electric muffle furnace at 175° C. for one hour and then calcining it at 750° C. for one hour. Metal precursor amounts are as follows: Ex 1—1.72 g gallium nitrate hydrate, 1.53 g aluminum nitrate hydrate and 0.13 g potassium nitrate; Ex 2—1.72 g gallium nitrate hydrate, 0.76 g aluminum nitrate hydrate and 0.13 g potassium nitrate; Ex 3—1.72 g gallium nitrate hydrate, 0.38 g aluminum nitrate hydrate and 0.13 g potassium nitrate; Ex 4—1.72 g gallium nitrate hydrate, 0.18 g aluminum nitrate hydrate and 0.13 g potassium nitrate; Ex 5—12.06 g gallium nitrate hydrate, 3.11 g aluminum nitrate hydrate and 0.15 g potassium nitrate; CEx D—1.72 g gallium nitrate hydrate and 0.13 g potassium nitrate; and CEx E—11.87 g gallium nitrate hydrate and 0.15 g potassium nitrate.

EX 6-8 AND CEX F

Replicate Ex 1-5 and CEx D-E with changes to prepare four catalysts using high purity $Al_2O_3$ (at least 99.5% pure, CATALOX™ 5/70, Sasol) as the support. Metal precursor amounts are as follows: Ex 6—1.72 g gallium nitrate hydrate, 1.78 g aluminum nitrate hydrate and 0.13 g potassium nitrate; Ex 7—1.72 g gallium nitrate hydrate, 0.89 g aluminum nitrate hydrate and 0.13 g potassium nitrate; Ex 8—1.72 g gallium nitrate hydrate, 0.44 g aluminum nitrate hydrate and 0.13 g potassium nitrate; and CEx F—1.72 g gallium nitrate hydrate and 0.13 g potassium nitrate.

EX 9-10

Replicate Ex 2-3 with changes to prepare two catalysts by sequentially loading first the gallium nitrate hydrate and potassium nitrate and second the aluminum nitrate hydrate precursors. After the first loading step with gallium and potassium precursors, age the obtained material for two hours at ambient temperature, dry the aged at 175° C. for one hr, and then calcine the dried material at 750° C. for 1 hour before loading the aluminum nitrate hydrate precursor. After completing the aluminum precursor loading, dry the material and calcine it in the same manner as after the first loading step.

TABLE 1

Metal oxide loading on catalyst

| | Weight % on Catalyst* | | | Ga:Al** |
|---|---|---|---|---|
| | $Ga_2O_3$ | $Al_2O_3$ | $K_2O$ | (mol/mol) |
| Bulk metal oxide catalysts) | | | | |
| CEx A | 68.3% | 31.7% | 0.0% | 1.2 |
| CEx B | 81.2% | 18.8% | 0.0% | 2.3 |
| CEx C | 89.6% | 10.4% | 0.0% | 4.7 |
| Supported catalysts using silica containing aluminum as a support (Siralox) | | | | |
| Ex1 | 2.1% | 1.0% | 0.3% | 1.2 |
| Ex2 | 2.2% | 0.5% | 0.3% | 2.3 |
| Ex3 | 2.2% | 0.3% | 0.3% | 4.7 |
| Ex4 | 2.2% | 0.1% | 0.3% | 9.8 |
| Ex5 | 13.2% | 1.8% | 0.3% | 4.0 |
| CEx D | 2.2% | 0.0% | 0.3% | — |
| CEx E | 13.2% | 0.0% | 0.3% | — |
| Supported catalysts using high purity aluminum as a support (Catalox) | | | | |
| Ex6 | 2.1% | 1.2% | 0.3% | 1.0 |
| Ex7 | 2.1% | 0.6% | 0.3% | 2.0 |
| Ex8 | 2.2% | 0.3% | 0.3% | 4.0 |
| CEx F | 2.2% | 0.0% | 0.3% | — |
| Sequential loading Supported catalysts using silica containing aluminum as a support (Siralox) | | | | |
| Ex9 | 2.2% | 0.5% | 0.3% | 2.3 |
| Ex10 | 2.2% | 0.3% | 0.3% | 4.7 |

*Based upon combined weight of $Ga_2O_3$, $Al_2O_3$, $K_2O$. When the support is present, the stated amounts of $Ga_2O_3$, $Al_2O_3$, $K_2O$ are those deposited on the support, with the support contributing the balance of the catalyst up to 100 wt %.
**Ratio excluding contribution from the support where present Catalyst Testing Admix 0.5 g of each catalyst with 1.0 g silicon carbide, then subject the catalyst to a number of dehydrogenation reaction/catalyst reactivation/catalyst rejuvenation cycles as detailed below. In the dehydrogenation reaction step, pass a feed stream (95 mole percent (mol %) propane and 5 mol % nitrogen through a catalyst for a period of 60 seconds at a temperature of 625° C. and a propane weight hourly space velocity (WHSV) of 8 reciprocal hours ($hr^{-1}$) under ambient pressure (e.g. one atmosphere). Collect data for propane conversion and propane selectivity approximately 6 seconds after initiating contact between the feed stream and the catalyst. After the 60 second period lapses, ramp reactor temperature to 730° C. at a rate of 20° C. per minute in the presence of helium (He) flowing through the catalyst at a rate of 120 standard cubic centimeters per minute (sccm). Maintain the temperature at 730° C. while contacting the catalyst with a simulated $CH_4$ combustion products stream (4 mol % oxygen, 8 mol % carbon dioxide, 16 mol % water vapor and 72 mol % He) at a flow rate of 150 sccm for a period of three minutes. Subsequent to treatment with the simulated combustion products stream, pass 100% air through the catalyst at a flow rate of 150 sccm for a period of 15 minutes. After air treatment and before starting another PDH reaction cycle, cool the reactor to the reaction temperature (625° C.) and stabililze the temperature of the system over a period of 20 min under flowing He (flow rate of 120 sccm) to effect stripping of labile oxygen from the catalyst and make the temperature of the catalyst bed substantially uniform before the next reaction/regeneration cycle.

Summarize catalyst test results for catalysts prepared in CEx A-C after 15, 30 and 50 cycles in terms of % propane ($C_3H_8$) conversion, % propylene ($C_3H_6$) selectivity and product % selectivity for propylene ($C_3H_6$ in Table 2 below. In Tables 3A-3C below, do the same for Ex 1-5, 9, 10, CEx D and CEx E.

The conversion, selectivity and yield are all based on mol %.

TABLE 2

| Cat/Cycle No | % $C_3H_8$ Conversion | % $C_3H_6$ Selectivity | % $C_3H_6$ Yield |
|---|---|---|---|
| A/15 | 40.3 | 71.5 | 28.8 |
| A/30 | 38.9 | 72.5 | 28.2 |
| A/50 | 38.0 | 72.9 | 27.7 |
| B/15 | 34.5 | 79.2 | 27.4 |
| B/30 | 32.6 | 80.1 | 26.1 |
| B/50 | 31.0 | 80.7 | 25.0 |
| C/15 | 37.2 | 78.2 | 29.1 |
| C/30 | 34.9 | 79.5 | 27.8 |
| C/50 | 32.7 | 83.9 | 27.4 |

TABLE 3A

| Cat/Cycle No | % $C_3H_8$ Conversion | % $C_3H_6$ Selectivity | % $C_3H_6$ Yield | Ga:Al* (mol/mol) | Weight % on Catalyst* | | |
|---|---|---|---|---|---|---|---|
| | | | | | $Ga_2O_3$ | $Al_2O_3$ | $K_2O$ |
| 1/15 | 42.2 | 94.0 | 39.7 | 1.2 | 2.1% | 1.0% | 0.3% |
| 1/30 | 40.4 | 93.7 | 37.9 | | | | |
| 1/50 | 37.7 | 93.2 | 35.1 | | | | |
| 2/15 | 52.1 | 95.0 | 49.5 | 2.3 | 2.2% | 0.5% | 0.3% |
| 2/30 | 51.1 | 94.9 | 48.5 | | | | |
| 2/50 | 49.1 | 94.8 | 46.6 | | | | |
| 3/15 | 43.6 | 93.8 | 40.9 | 4.7 | 2.2% | 0.3% | 0.3% |
| 3/30 | 45.6 | 94.0 | 42.9 | | | | |
| 3/50 | 45.6 | 94.0 | 42.9 | | | | |
| 4/15 | 39.7 | 94.7 | 37.6 | 9.8 | 2.2% | 0.1% | 0.3% |
| 4/30 | 41.2 | 94.8 | 39.1 | | | | |
| 4/50 | 40.9 | 94.7 | 38.8 | | | | |

*Refers to the amount of Ga, Al, K added to the support.

TABLE 3B

| Cat/Cycle No | % $C_3H_8$ Conversion | % $C_3H_6$ Selectivity | % $C_3H_6$ Yield | Ga:Al* (mol/mol) | Weight % on Catalyst* | | |
|---|---|---|---|---|---|---|---|
| | | | | | $Ga_2O_3$ | $Al_2O_3$ | $K_2O$ |
| 5/15 | 29.6 | 87.8 | 26.0 | 4.0 | 13.2% | 1.8% | 0.3% |
| 5/30 | 28.4 | 88.0 | 25.0 | | | | |
| 5/50 | 27.2 | 87.8 | 23.9 | | | | |
| 6/15 | 42.4 | 93.3 | 39.5 | 1.0 | 2.1% | 1.2% | 0.3% |
| 6/30 | 44.0 | 93.5 | 41.2 | | | | |
| 6/50 | 44.4 | 93.6 | 41.5 | | | | |
| 7/15 | 42.2 | 93.7 | 39.5 | 2.0 | 2.1% | 0.6% | 0.3% |
| 7/30 | 44.1 | 93.9 | 41.4 | | | | |
| 7/50 | 45.4 | 94.1 | 42.8 | | | | |
| 8/15 | 39.0 | 93.3 | 36.4 | 4.0 | 2.2% | 0.3% | 0.3% |
| 8/30 | 40.0 | 93.4 | 37.4 | | | | |
| 9/15 | 37.4 | 93.4 | 35.0 | 2.3 | 2.2% | 0.5% | 0.3% |
| 9/30 | 38.9 | 93.5 | 36.4 | | | | |
| 9/50 | 38.2 | 93.5 | 35.7 | | | | |

TABLE 3B-continued

| Cat/Cycle No | % $C_3H_8$ Conversion | % $C_3H_6$ Selectivity | % $C_3H_6$ Yield | Ga:Al* (mol/mol) | Weight % on Catalyst* $Ga_2O_3$ | $Al_2O_3$ | $K_2O$ |
|---|---|---|---|---|---|---|---|
| 10/15 | 39.8 | 94.7 | 37.7 | 4.7 | 2.2% | 0.3% | 0.3% |
| 10/30 | 41.8 | 94.8 | 39.6 | | | | |
| 10/50 | 43.3 | 94.8 | 41.1 | | | | |

*Refers to the amount of Ga, Al, K added to the support.

TABLE 3C

| Cat/Cycle No | % $C_3H_8$ Conversion | % $C_3H_6$ Selectivity | % $C_3H_6$ Yield | Ga:Al* (mol/mol) | Weight % on Catalyst* $Ga_2O_3$ | $Al_2O_3$ | $K_2O$ |
|---|---|---|---|---|---|---|---|
| D/15 | 29.4 | 91.8 | 27.0 | — | 2.2% | 0.0% | 0.3% |
| D/30 | 28.8 | 91.7 | 26.4 | | | | |
| D/50 | 27.6 | 91.3 | 25.2 | | | | |
| E/15 | 26.1 | 88.3 | 23.1 | — | 13.2% | 0.0% | 0.3% |
| E/30 | 26.5 | 88.7 | 23.5 | | | | |
| E/50 | 26.2 | 89.3 | 23.4 | | | | |
| F/15 | 33.5 | 92.2 | 30.9 | — | 2.2% | 0.0% | 0.3% |
| F/30 | 35.7 | 92.1 | 32.9 | | | | |
| F/50 | 37.2 | 92.4 | 34.4 | | | | |

*Refer to the amount of Ga, Al, K added to the support.

The data presented in Tables 2 and 3A through 3C provide support for a number of observations. First, as shown in Table 2, bulk mixed metal oxides, even with $Ga_2O_3$ loadings in excess of 65 wt % (see Table 1 for CEx A-C), provide a propane conversion of no more than 40.3% (Table 2, CEx A, 15 cycles). Second, also as shown in Table 2, the maximum selectivity to propylene for bulk mixed metal oxides is 83.9% (Table 2, CEx C, 50 cycles). Third, Table 3C shows that propane conversion, propylene selectivity and propylene yield are somewhat higher for a relatively low $Ga_2O_3$ loading (2.2 wt % for CEx D) than for a relatively higher $Ga_2O_3$ loading (13.2 wt % for CEx E). Fourth, addition of $Al_2O_3$ to the active layer (along with the $Ga_2O_3$), either in a one-step procedure (Ex 1-5) or a sequential procedure (Ex 9-10), leads to a marked increase in propylene selectivity relative to what one can obtain with bulk mixed metal oxides where the same oxides are used but with $Ga_2O_3$ loadings significantly lower for the supported catalysts than for the bulk mixed metal oxides. Fifth, the amount of $Al_2O_3$ included in the active layer also affects catalyst performance, with a Ga/Al molar ratio preferred to range from greater than 0.5:1 to less than 15:1, and more preferably 1:1 to less than 10:1, and most preferably 1.5:1 to 5:1. For catalyst to have good activity and selectivity, gallium oxides loading is preferably to be greater 0 wt % and lower than 14 wt %, and more preferably be greater 0 wt % and lower than 10 wt %, and most preferably greater 0 wt % and lower than 5 wt %.

What is claimed is:

1. A heterogeneous alkane dehydrogenation catalyst consisting of a combination of aluminum oxide and gallium oxide dispersed as an active layer on a silica-modified alumina support.

2. The catalyst of claim 1, wherein the aluminum and the gallium in the active layer are present in a molar ratio of gallium to aluminum that is within a range of from greater than 0.5:1 to less than 15:1.

3. The catalyst of claim 2, wherein the molar ratio is within a range of from 1:1 to 10:1.

4. The catalyst of claim 1, wherein the aluminum oxide in the active layer is present in an amount within a range of from 0.05 percent by weight to 14 percent by weight and the gallium oxide in the active layer is present in an amount within a range of from greater than 0 percent by weight to less than fourteen by weight, each weight percent being based upon total catalyst weight.

5. The catalyst of claim 4, wherein the amount of aluminum oxide is within a range of from 0.05 percent by weight to 5 percent by weight and the gallium oxide is present in an amount within a range of from greater than 0 percent by weight to less than seven percent by weight, each weight percent being based upon total catalyst weight.

6. The catalyst of claim 1, comprising the silica-modified alumina support comprising from 0.1 wt. % to 10 wt. % silica based on the total weight of the support.

7. A heterogeneous alkane dehydrogenation catalyst consisting of a combination of aluminum oxide and gallium oxide dispersed as an active layer on an alumina support or a silica-modified alumina support, wherein the aluminum and the gallium in the active layer are present in a molar ratio of gallium to aluminum that is within a range of from greater than 0.5:1 to less than 15:1.

8. The catalyst of claim 7, wherein the molar ratio is within a range of from 1:1 to 10:1.

9. The catalyst of claim 7, wherein the aluminum oxide in the active layer is present in an amount within a range of from 0.05 percent by weight to 14 percent by weight and the gallium oxide in the active layer is present in an amount within a range of from greater than 0 percent by weight to less than fourteen by weight, each weight percent being based upon total catalyst weight.

10. The catalyst of claim 9, wherein the amount of aluminum oxide is within a range of from 0.05 percent by weight to 5 percent by weight and the gallium oxide is present in an amount within a range of from greater than 0 percent by weight to less than seven percent by weight, each weight percent being based upon total catalyst weight.

11. A catalyst comprising a support and an active layer dispersed on the support, the active layer comprising aluminum oxide and gallium oxide, wherein a molar ratio of gallium to aluminum in the active layer is from 0.5:1 to 15:1.

12. The catalyst of claim 11, wherein the support is an inactive support.

13. The catalyst of claim 11, wherein the support is an alumina support or a silica-modified alumina support.

14. The catalyst of claim 13, wherein the support is a silica-modified alumina support comprising from 0.1 wt. % to 10 wt. % silica based on the total weight of the support.

* * * * *